United States Patent [19]

Novotny et al.

[11] Patent Number: 4,479,380
[45] Date of Patent: Oct. 30, 1984

[54] OPEN-TUBULAR SUPERCRITICAL FLUID CHROMATOGRAPHY

[75] Inventors: Milos Novotny, Bloomington, Ind.; Milton L. Lee, Spanish Fork, Utah; Paul A. Peaden; John C. Fjeldsted, both of Provo, Utah; Stephen R. Springston, Bloomington, Ind.

[73] Assignee: Brigham Young University, Provo, Utah

[21] Appl. No.: 352,890

[22] Filed: Feb. 26, 1982

[51] Int. Cl.³ .............................................. G01N 31/08
[52] U.S. Cl. .................................................. 73/61.1 C
[58] Field of Search ........................... 73/61.1 C, 23.1; 422/70, 89

[56] References Cited

U.S. PATENT DOCUMENTS

| | | | |
|---|---|---|---|
| 4,124,358 | 11/1978 | Müller | 73/61.1 C |
| 4,151,741 | 5/1979 | Schirrmeister | 73/23.1 |
| 4,271,695 | 6/1981 | Sisti et al. | 73/23.1 |

OTHER PUBLICATIONS

T. Tsuda et al., "Packed Microcapillary Columns in High Performance Liquid Chromatography", Anal. Chem., vol. 50, No. 2, pp. 271-275, Feb. 1978.
T. H. Gouw & R. E. Jentoft, Supercritical Fluid Chromatography, vol. 68, 1972, pp. 303-323, J. Chromatography.
R. E. Jentoft & T. H. Gouw, Pressure-Programmed Supercritical Fluid Chromatography of Wide Molecular Weight Range Mixtures, vol. 8, 1970, pp. 138-142, J. Chromatography Sci.
J. E. Conway, J. A. Graham & L. B. Rogers, Effects of Pressure, Temperature, Adsorbent Surface, and Mobile Phase Composition on the Supercritical Fluid Chromatographic Fractionation of Monodisperse Polystyrenes, vol. 16, 1978, J. Chromatography Sci.
W. Asche, Mobile Phases for Supercritical Fluid Chromatography, vol. II, 1978, pp. 411-412, Chromatographia.

Primary Examiner—Stephen A. Kreitman
Attorney, Agent, or Firm—George H. Mortimer

[57] ABSTRACT

Apparatus for and method of open-tube supercritical fluid chromatography. The apparatus comprises an elongated passageway having inlet and outlet ends such as a capillary column, coated or not with a coating having affinity for solute molecules to be analyzed, means such as a high-pressure pump operatively connected to an electronic pressure controller/programmer for supplying fluid at high pressure to said inlet end, means such as a flow controller/restrictor for removing fluid from said outlet end, means such as a constant temperature oven for subjecting the fluid between said inlet and outlet ends to a temperature near (below, at or above) the critical temperature of the fluid, means for introducing a sample material into the fluid upstream from the inlet end for chromatographic analysis, such means preferably being an injector of the split injection type or optionally of the on-column type, and means for subjecting fluid to which a sample material has been added to detection by means of an ultraviolet detector, an on-column spectrofluorimeter, a mass spectrmeter, and the like. The method comprises carrying out the detection of material after subjecting it to supercritical fluid chromatography in a long stream of fluid, preferbly of capillary diameter, having an inlet end and an outlet end and which is subjected between said ends to near supercritical temperature and pressure for the fluid, the detection being carried on the fluid out near the outlet end by any suitable method including ultraviolet detection, spectrofluorimetric detection and mass spectrometric detection.

24 Claims, 7 Drawing Figures

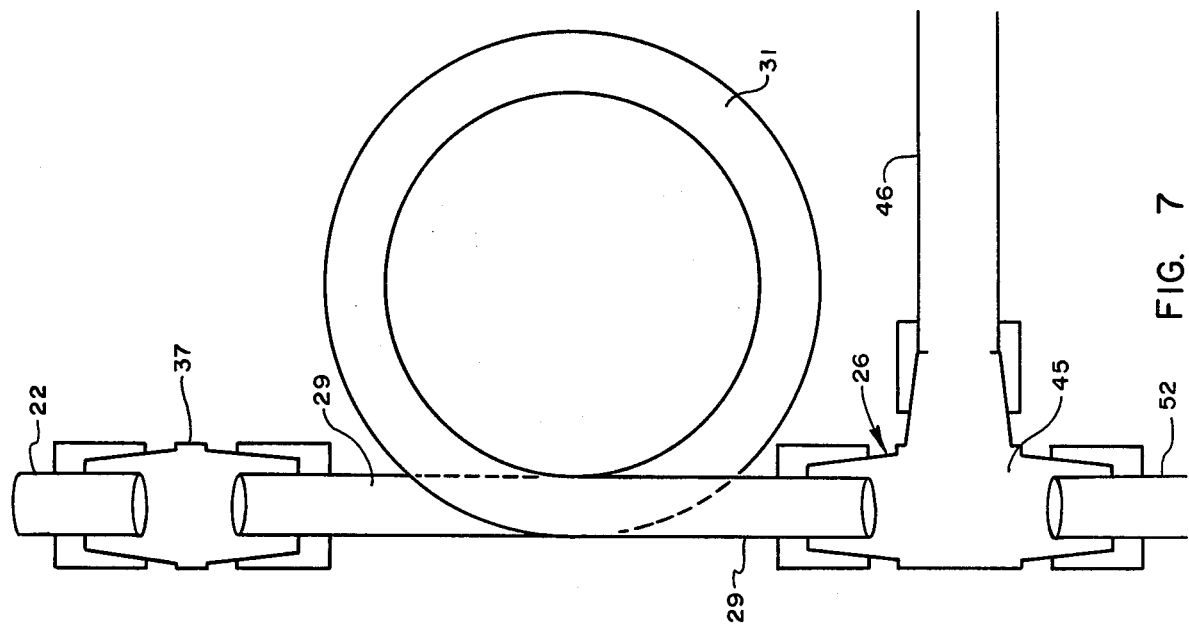
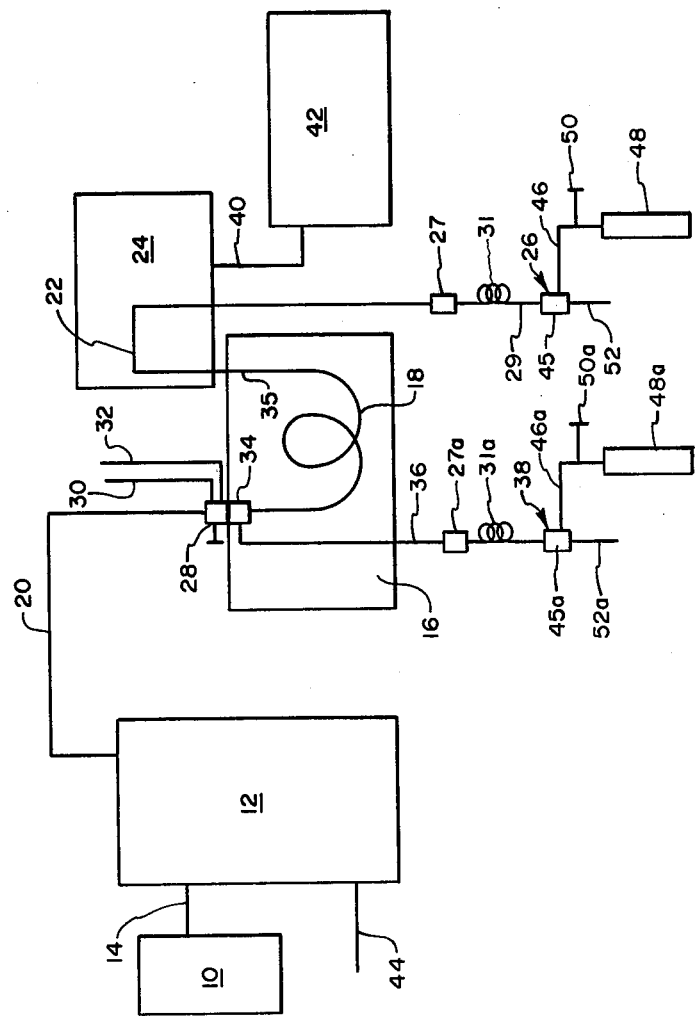

OPEN-TUBULAR SUPERCRITICAL FLUID CHROMATOGRAPHY

INTRODUCTION

The present invention relates to supercritical fluid charomatography, and more particularly to the use of open-tubular (capillary) columns in supercritical fluid chromatography. In supercritical fluid chromatography the mobile phase is neither a gas nor a liquid but is a fluid subjected to pressures and temperatures near its critical point. Under these conditions the density of a supercritical fluid approaches that of a liquid but its solute diffusion coefficients are approximately two orders of magnitude greater than those found in liquids. A supercritical fluid possesses solvating properties similar to a liquid while its solute diffusivities lie between those of gases and liquids. The present invention uses a supercritical fluid in an elongated open confined passageway, preferably of capillary dimension, e.g., a circular tube having an internal diameter less than 1 millimeter, at a suitable temperature and with pressure programming to separate relatively non-volatile and/or thermally labile solutes. The invention has its greatest utility in separating such solutes which cannot be analyzed by gas chromatography or, in many cases, by liquid chromatography, but it may be utilized in separating such solutes which can be analyzed by gas and/or liquid choromatography.

BACKGROUND OF THE INVENTION

Supercritical fluid chromatography has been reported by T. H. Gouw and R. E. Jentoft in J. Chromatogr., Vol. 68, pages 303-323, 1972, but with a packed column as an essential component of the system. Packed columns have some inherent problems that limit their usefulness. Among these problems are the large pressure drop along the column which limits the length of column that is practicable and the density gradient in the fluid which the pressure drop make inevitable. Another problem is the plate height contributions due to alternate solvent flow paths that are present in packed columns.

Open tubular confined passageways, including those of capillary dimensions, are available commercially but they have not been used for supercritical fluid chromatography.

Temperature programming is used to modify solute retention in gas chromatography. In supercritical fluid chromatography liquid formation is prevented by operating at constant temperature near or above the critical temperature of the fluid and the mobile phase density is controlled by adjusting the pressure. Pressure programming has been reported for controlling the density of the fluid used in supercritical fluid chromatography by R. E. Jentoft and T. H. Gouw in J. Chromatogr. Sci., Vol. 8, pages 138-142, 1970, and by J. E. Conway, J. A. Graham and L. B. Rogers in J. Chromatogr. Sci., Vol. 16, pages 102-110, 1978. A gradual increase in pressure gradually increases the mobile phase density but not in a linear relation. Increased mobile phase density decreases solute retention.

W. Asche has stated that a number of different mobile phases may be used in supercritical fluid chromatography in Chromatographia, Vol. 11, pages 411-412, 1978.

SUMMARY OF THE INVENTION

The present invention has both apparatus and method aspects. The apparatus comprises a plurality of elements or modules, including an enlongated open confined passageway which may be of capillary dimension, combined in a unique way to produce a new separation device of paricular uitility in cases described hereinafter. The method involves chromatographically separating relatively non-volatile and/or thermally labile solutes and subjecting the separated material to detection. It has its greatest utility in separating such solutes which cannot be analyzed by gas chromatography or, in many cases, by liquid chromatography but also may be used advantageously with solutes which may be analyzed by gas and/or liquid chromatography.

BRIEF DESCRIPTION OF THE DRAWINGS

The invention will be described and illustrated in conjunction with the drawings in which:

FIG. 1 is a schematic representation of the best known embodiment of the apparatus of the invention;

FIG. 7 is a diagrammatic representation of a flow controlling means useful in the invention.

DETAILED DESCRIPTION OF THE APPARATUS AND METHOD

Figure 2:
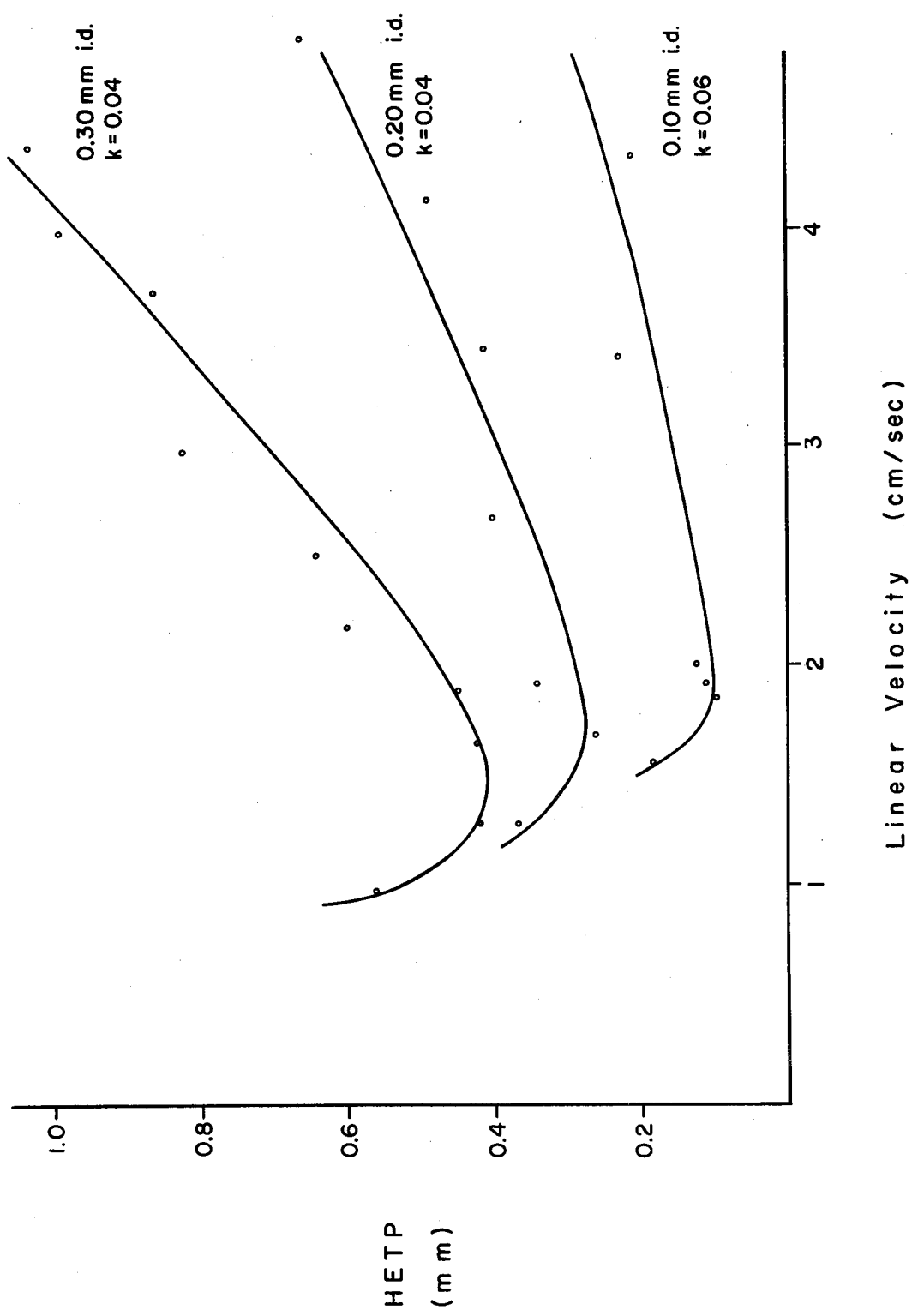
FIG. 2 is a van Deemter plot for naphthalene comparing columns of 0.30, 0.20 and 0.10 millimeter internal diameter using the split sampling method.

The apparatus of the invention is a combination of elements or modules which are operatively connected in a unique way to achieve heretofore unattainable results. These elements or modules include an elongated open confined passageway having inlet and outlet ends, means for supplying a mobile fluid to the inlet end of the passageway under supercritical variable controllable pressure, means for heating the passageway and the fluid in it to a controlled temperature near or above the critical temperature, means for introducing samples into the inlet of said passageway, means for detecting the presence in the fluid flowing near the outlet end of the passageway of any compound or representative compound that has been introduced into the passageway, and a flow controller for releasing fluid from the outlet end of the passageway. The means for introducing samples into said inlet end of the passageway may be an on-column injector but preferably is a split injector which utilizes and variable flow controller to split or partition the sample liquid in a controllable ratio between the capillary and discharge means to vent excess sample liquid from the injector.

Referring now to the drawing, the means for supplying a mobile fluid to the inlet end of the passageway under supercritical variable controlled pressure preferably comprises an electronic pressure controller and programmer 10, a high pressure pump 12 and any suitable means 14 for operatively connecting modules 10 and 12. The means for heating the passageway and the fluid in it preferably comprises a temperature regulated oven 16. Within the oven an elongated open confined passageway 18 is suitably mounted. This passageway 18 may be a capillary column or coil having an inlet end connected to a connector 34 and an outlet end 35. The connector 34 is connected to a split injector housing 28 by a short length of tubing 20 and housing 28 in turn is connected to module 12 by a suitable length of tubing 20. The outlet end 35 of the passageway 18, when combined with certain types of detecting means, passes into the means 24, but, when combined with other types of detecting means, connects to the inlet side thereof, for detecting the presence in the fluid flowing in or from the outlet 35 of passageway 18 of any compound or representative compound that has been introduced into the passageway. Tubing 22 is either connected to outlet end 35 or to the outlet side of those certain types of detecting means referred to above for detecting components removed from passageway 18. In tubing 22 downstream from the detecting means 24 is a flow controlling means 26 for releasing fluid from the outlet end 35 of the passageway 18 at a controllable rate. In some cases that tubing 22 may be simply a continuation of the capillary column of which passageway 18 is made, but in general it is preferred that tubing outside the detecting means 24 be made of more rugged tubular material. Where a detecting means is used that detects material removed from the column, the more rugged tubular material 22 connects to the outlet side thereof. Stainless steel tubing is a good example of more rugged tubing than glass or fused silica which are common materials used in making capillary columns.

Figure 6:
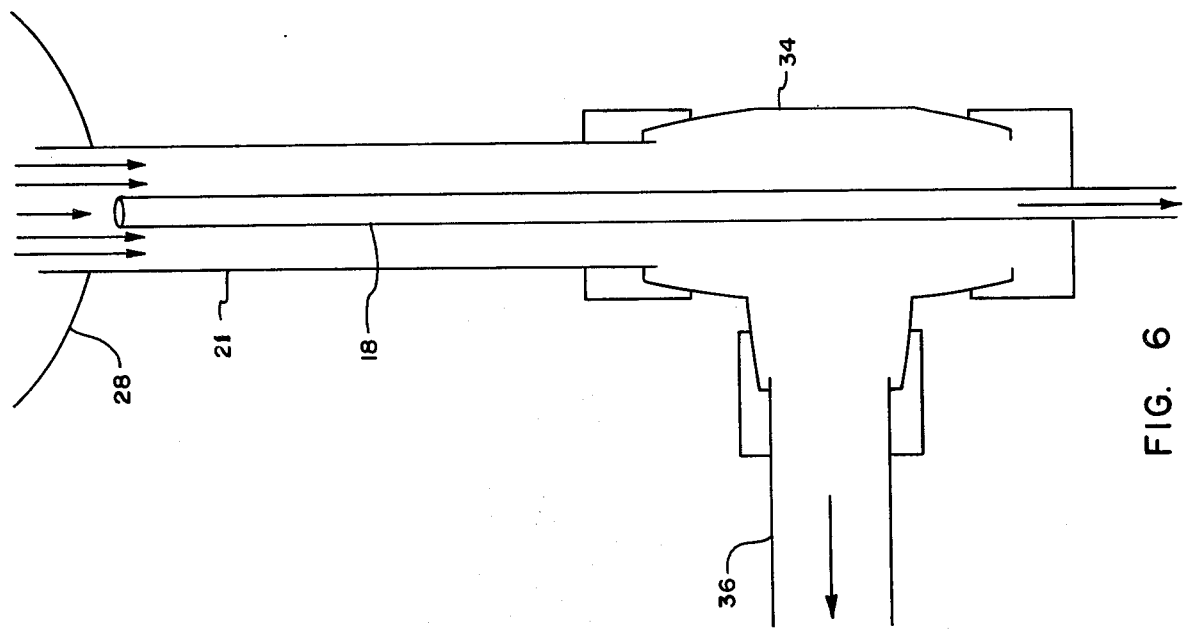
FIG. 6 is a diagrammatic representation of a splitter injector useful in the invention.

The split injector means for introducing samples of material to be analyzed comprises the housing 28 and the connected tubing 21 which is concentrically located around the inlet end of passageway 18 just at the outlet of 28, as seen in FIG. 6. Connector 34 is a tee, preferably a Swagelok tee, having its upper port connected to tube 21, its lower port connected to passageway 18 and its side port to tubing 36 for discharging, under control of a flow controller 38, that part of the liquid solution leaving housing 28 which does not enter the passageway 18.

Means 40 represents an operative connection of module to a data logging means 42 which has significant benefit in the system. Means represented by number 44 provides an operative connection of the pump 12 to a supply of fluid material (not shown).

The module 10 may comprise any electronic circuitry which will interact with the high pressure pump in such a way as to regulate the pressure of the fluid being introduced into the passageway 18. The term "programmer" is used to mean that the electronic control circuitry preferably will be programmable so that the desired operating pressure of the system can be varied in any predetermined way. A suitable electronic circuit is disclosed by F. J. Van Lenten and L. Rothman in Anal. Chem., Vol. 48, pages 1430-1432, 1976.

The module 12 comprises any pump system or apparatus capable of delivering a fluid at a pressure within the range of 10 to 250 atmospheres. Among commercially available pumps, any of which may be used with good results, are the following: Varian Model 8500 syringe pump disclosed in its Chromatography Catalog No. 19, page 24, and which bears the designation SEP (Printed in USA 43M1-78).

Perkin Elmer Series 1 pump disclosed in its catalog bearing a 1978 copyright date and the designations Order No. L-544, April 1918, AD117810.

Perkin Elmer Series 2/1 and 2/2 delivery systems disclosed in its catalog bearing a 1977 copyright date and designations Order No. L-494, April 1977, CP4/77/25. These systems also have sample injection capablity.

Perkin Elmer Series 3B solvent delivery system described in its catalog bearing a 1979 copyright date designations Order No. L-495A, August 1979, ACP87920.

Altex Model 100A solvent metering pump as disclosed in its catalog bearing designation 90/2-78/15M.

Chromatix Model 600/200 HPLC contant flow pump as disclosed in its catalog bearing the designation 8M-11-78.

The means for heating the passageway and the fluid in it may be any suitable commercially available oven or the like capable of producing a certain temperature, whether the desired temperature is isothermal or varied. Among the commercially available ovens which are suitable are the following:

Hewlett Packard model 5700A GC oven as described in its 1982 catalog of Electronic Instruments And Systems, page 730.

Varian model 3700 oven as described in its Gas Chromatography Catalog No. 21, pages 12 et seq., which bears the designation SEP-2549 (Printed in USA).

Perkin Elmer Sigma B series gas chromatography ovens as described in its catalog which bears the designation K10-59-01926 (Printed in England).

Perkin Elmer LC-100 column oven as described in its catalog bearing the designations Order No. L-551, May 1978, EP7/78 5.

The passageway 18 consists of any small diameter open bore tubular passageway or column, e.g., an internal diameter less than 1 mm. It is advantageous in some cases to coat the internal wall of this passageway with one of several materials having variable affinities for solute molecules to be analyzed and separated using a supercritical fluid or dense gas as the mobile phase. Such a coating should have the following characteristics:

a. It should be insoluble in the mobile phase.

b. It should form a stable film on the inner wall surface, i.e., it should not decompose or flow on the surface to form droplets.

c. It should behave well chromatographically, i.e., it should not interfere with the chromatographic analysis. Among suitable coating materials are methyl and phenyl silicone polymers and adsorbents such as silica, alumina and activated carbon. Capillary columns manufactured by the following companies are suitable:

Alltech capillary columns as described in its catalog No. 33,1979.

Chormatech capillary columns as described in its catalog G.C.1978/200.

J & W Durabond fused silica capillary columns as described in its catalog High Resolution Chromatograph Products, bearing a 1980 copyright notice.

SGE capillary columns as described in its catalog bearing a 1979 copyright date.

The detecting means 24 may be any system capable of detecting the presence in the fluid near the outlet of the passageway of any compound or representative compound that has been introduced into the passageway 18. Such systems include ultraviolet detectors, spectrofluorimeteric (sometimes called fluorescence) detectors, infrared absorption detectors and mass spectrometers. In those systems involving transmission of rays through the wall of the container for the fluid in the zone of detection, the container or passageway for the fluid should be transparent to the rays of the detecting means. Where the column is glass or fused silica, the zone of detection may simple be part of the column near the outlet. It is advantageous to narrow the illuminating beam to a thickness approximately equal to the internal diameter of the column at the zone of detection, e.g., by passing the beam through a slit of proper dimension. Where the zone of detection is a different vessel, as with mass spectrometers, the vessel should be connected to the outlet end 35 of the passageway at its inlet side. Among the several commercial detectors which are satisfactory are the following:

Perkin Elmer model 204A spectrofluorimeter as described in its MANUAL OF INSTRUCTIONS, Part No. 204-1095, December 1977.

Kratos model 770 UV monitor and model FS-970 fluorescence detector as described in its catalog bearing a 1978 copyright date in the name of Kratos Inc., Schoeffel Instrument Division.

Miran model 1A cvf Ir absorption detector as described in its catalog bearing a 1980 copyright date of the Foxboro Company and the designation Bulletin L-17B-5M-0480.

Varian gas chromatograph detectors as described in its catalog identified above, page 143.

Hewlett Packard model 5985B mass spectometer as described in its catalog identified above, page 731.

The means 28 may be any suitable device which facilitates introduction of samples to be chromatographed into the passageway 18. Among suitable commercailly available devices are the following:

Schoeffel model 7120 sample injector as described in its catalog of HPLC Injection Valves.

Valco stainless steel injection valves-internal volume, as described in its catalog designated as VAL 027.

In addition to commercially available split injectors, a split injector built in accordance with the principle illustrated in FIG. 6 as described above is very satisfactory. Part 28 is the casing or housing of the valve seen FIG. 1. By turning the handle of the valve to "on" position, sample-containing fluid enters the valve body from the supply through tubing 30 until the valve is turned off from that supply. Any excess fluid is vented thorugh tubing 32. The desired volume for chromatographic analysis flows under the pressure generated by pump 12 out of the casing 28 into the splitting means comprising the inlet end of column 18 and the tubing 21. The ratio of the split depends upon the back pressures in the two respective open tubular members. The operation of the split injector will be described more fully in conjunction with FIG. 7 hereafter.

The flow controllers 26 and 38 may be of the same or different construction provided each is capable of establishing or assisting in establishing the flow of mobile phase, sample or any other fluid through the chromatographic system, whether it pertains to flow rates, sample introduction, a detection process/interface or any other aspect related to the system. Satisfactory flow controllers for use in the apparatus of the invention include the following:

A flow controller built in accordance with the principle disclosed in FIG. 7 in which the controller is designated generally by number 26 and comprises a connector 27, e.g., a Swagelok connector, making fluid-tight connection at one end either to tubing 22 to which the outlet end of column 18 is either connected or, if desired, tubing 22 may be omitted and the end of column 18 connected directly, but less preferably, to the said end of fitting 27 while the other end makes fluid-tight connection with tubing 29 which is preferably coiled at 31 to lengthen the path of flow of the fluid in it without greatly extending the size of the apparatus. The other end of tubing 29 makes fluid-tight connection to tee 45 at the upper port thereof while the horizontal tee port makes fluid-tight connection to tubing 46 which is connected at the other end to a gas pressure tank 48 through a valve 50. The downwardly facing tee port makes fluid-tight connection to tubing 52 which may be any desired length to provide the necessary back pressure on the fluid flowing through it and which may be controlled by regulating the degree of opening of the valve 50.

Flow controller 38 is illustrated as having the same construction as 26 and parts are designated by the same reference numbers with the postscript "a" so that further description of it is not necessary for full and complete disclosure. It is the variable control of back pressure in Swagelok tee 45a which enables an operator to adjust the relative fluid flowrates in tubes 18 and 21 at the outlet of 28 to make the desired split at that point between the sample which flows into the column 18 and that which flows past it to discharge tube 52a.

In addition to the flow controller just described, the following references disclose satisfactory alternative choices:

E. Klesper and W. Hartman, Europ. Polym. J., Vol. 14, pages 77-88, 1978.

R. E. Jentoft and T. H. Gouw, Vol. 44, pages 681-686, 1972.

N. M. Karayannis, A. H. Corwin, E. W. Baker, E. Klesper and J. A. Walter, Anal. Chem., Vol. 40, pages 1736-1739, 1978.

Data logging means 42 comprises any means or system whereby the signals of conditions of the modules 10, 12, 16, 24, 26 and 38 are monitored. Commercially available devices which are suitable in the present invention include the following:

Houston Instruments chart recorder model 4950-1 as desribed in its INSTRUCTION MANUAL designated as I-1891279.

Linear Instruments chart recorder model 453 as described in Analabs' catalog of Chromatography Chemicals and Accessories, Bulletin K-22 058145, page 99.

Hewlett Packard model 9845 desktop computer as described in its catalog identified previously, page 35.

The method of the invention involves carrying out supercritical fluid chromatography by a combination or a series of steps or operations comprising supplying fluid near its critical pressure to an elongated open tube having an inlet end and an outlet end heated between the inlet and outlet ends near the critical temperature of said fluid, introducing into the fluid upstream from said inlet end of said open tube a sample of material to be analyzed, which material is separated chromatographically as it passes through the heated tube, and subjecting said fluid and contained sample near the outlet or upon removal thereof from the outlet end of said open tube.

The introduction of the sample into the fluid can be carried out by on-column injection. One satisfactory way of carrying out such injection comprises dissolving the sample in a suitable solvent and injecting the sample into the open tube at a temperature substantially lower than the critical temperature of the fluid in the open tube, subsequently raising the temperature to near the critical temperature of said fluid, and then ramping up the pressure in said open tube to the desired operating pressure. Another satisfactory way of carrying out such injection comprises dissolving the sample in a suitable solvent, injecting the solvent and the dissolved sample into the fluid at a temperature near the critical temperature and raising the pressure in said open tube to the operating pressure. In this method of injection, the solvent may be the same material as the fluid used in the open tube.

The step of sample detection near or just after fluid removal from the outlet end of the heated open tube may be carried out in any suitable manner. A desirable manner is on-column fluorescence detection. A description of this process of detection is described in the following articles:

M. Novotny, S. R. Springston, P. A. Peaden, J. C. Fjeldsted and M. L. Lee in Anal. Chem., Vol. 53, pages 407A–414Am, 1981.

F. J. Yang in Chromatogr. Commun., Vol. 4, pages 83–85, 1981.

J. W. Jorgenson and K. D. Lukacs, in Anal. Chem., Vol. 53, pages 1298–1302, 1981.

Analyses of carbon black extract and coal tar were made using n-pentane as the mobile phase in apparatus of the invention which comprised modules as illustrated in the drawing in which module 12 was the Varian 8500 syringe pump referred to hereinabove together with module 10 utilizing the circuitry described in the Van Lenten and Rothman article (Op.cit, supra), module 16 was the Hewlett Packard 5700A oven without its conventional injection port and detector, module 24 was the Perkin Elmer 204-A spectrofluorimeter described above which was mounted above the oven and a stainless steel block designed to hold the outlet end of the column 18 in proper alignment for on-column detection was used in place of the conventional fluorescence detector flow cell. Room temperature was used for some sample injections using the apparatus illustrated in FIG. 6 using Valco 0.2 μL valve CFSV-4-HPa 0.2 μL described above. For injecting heated samples, Valco valves CFSV-4HTAX-N60 with 0.5 μL and 0.2 μL volumes were used and the structure illustrated in FIG. 6 was modified by the addition of a preheater having a 1 meter coil of 1 millimeter internal diameter stainless steel tubing positioned inside the oven to preheat the mobile phase before it reached the valve which was mounted approximately 3.8 centimeters from the wall, inside the oven, with the handle extended to the outside.

In order to maintain column pressure, two alternative forms of restrictor were used. One consisted of a length of 35 μm or 50 μm internal diameter pyrex tubing connected at the end of the passageway 18 immediately after module 24. The length of the restrictor determined the column flow rate and was chosen appropriately for the analytical column diameter being used. The other consisted of the shorter restrictor 26 (FIGS. 1 and 6) at the end of tubing 22, 48 was a high pressure nitrogen regulator (variable to 1500 pounds per square inch) and 52 was a relatively short second restrictor so that the pressure in the tee did not increase above that of the nitrogen head pressure applied.

The passageway 18 used consisted of a pyrex glass capillary column which had been provided with a bonded polyethylphenylsiloxane stationary phase similar to that reported by L. Blomberg and T. Wannman in J. Chromatogr., Vol. 168, pages 81–88, 1979. This phase was a polymeric bonded phase providing greater flim thickness than the typical HPLC surface bonded phases obtained by surface silylation which have been used in packed-column SFC studies described by R. E. Jentoft and T. H. Gouw in Anal. Chem., Vol. 48, pages 2195–2200, 1976. The polymer for this bonded phase was synthesized by a procedure similar to that reported by L. Blomber et al, op.cit.supra.

Figure 4:
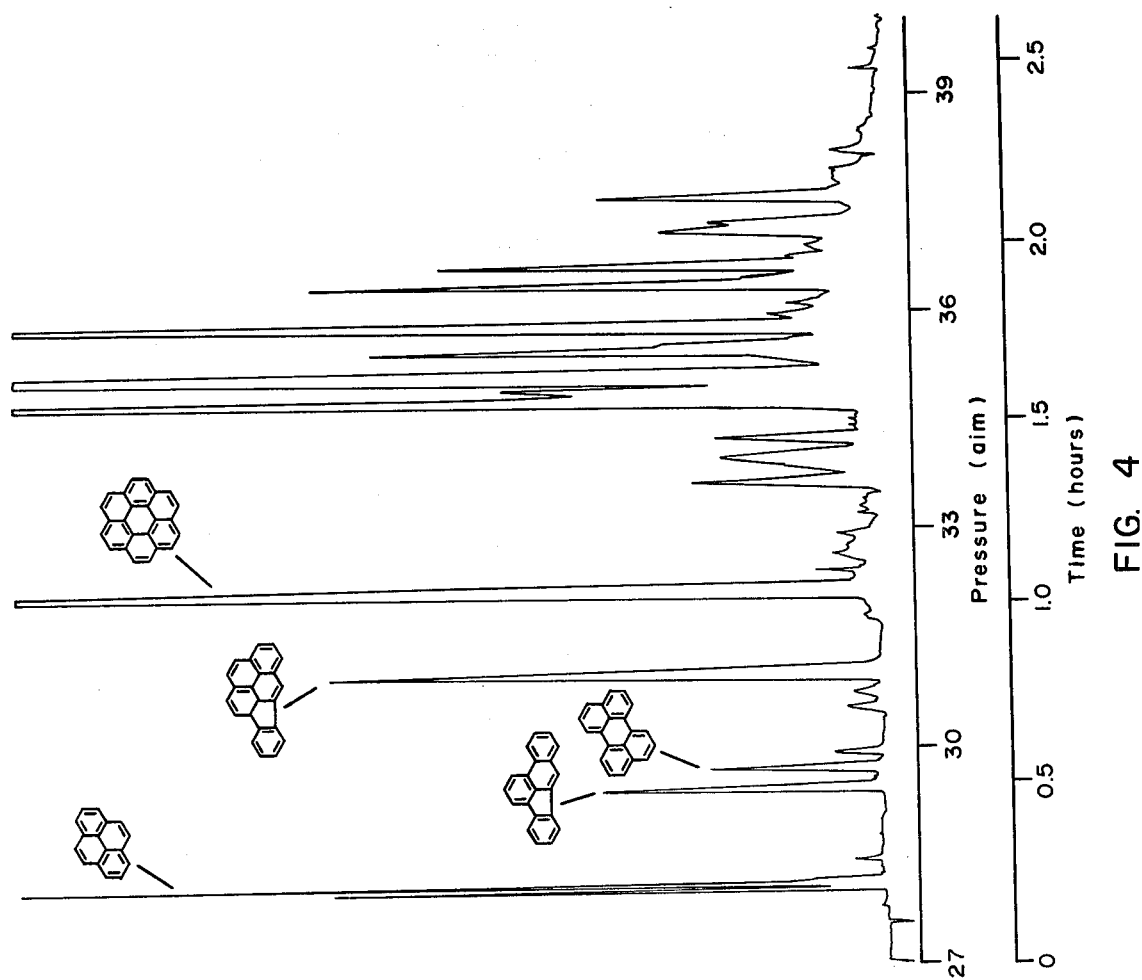
FIG. 4 is a copy of a chromatogram which demonstrates the application of capillary SFC to the separation of high-molecular-weight components in a carbon black extract.

In analyzing the carbon black a methylene chloride extract was chromatographed on an open-tubular column coated with a mixture of 75% cyanopropyl silicone fluid and 25% methyl silicone fluid which was 60 meters long and 0.13 millimeter in internal diameter using n-pentane as the mobile phase. The column temperature was 210° C. and the pressure was programmed from 27 atmospheres to 40.3 atmospheres at 5 atmospheres per hour. Injection was accomplished without splitting using a heated 0.2 μL valve and 1,2,4-trichlorobenzene as the solvent. Excitation and emission wave lengths were 335 and 450 nm, respectively. The chromatogram is copied in FIG. 4.

The analysis of asphalt and other similar samples using packed-column supercritical fluid chromatography has been reported by T. H. Gouw and R. E. Jentoft in Chromatogr. Sci., Vol. 11, pages 313–327, 1979. The same extract of carbon black has been analyzed and reported using conventional HPLC chromatography by P. A. Peaden, M. L. Lee, Y. Hirata and M. Novotny in Anal. Chem. Vol. 52, pages 2268–2271, 1980, and using capillary HPLC and capillary gas chromatography by Y. Hirata, M. Novotny, P. A. Peaden and M. L. Lee in Anal. Chim. Acta, Vol. 127, pages 55–61, 1981. A comparison of the results obtained by the method of the present invention with the results of the other methods shows its suitability. Moreover, in this process polycyclic aromatic compounds containing up to 11 rings were separated, showing the practical application of this prosess to the analysis of high-molecular weight compounds.

Coal tár was analysed by SFC on a 50 meter long capillary column having an interal diameter of 0.11 millimeters having a bonded polymethylphenyl stationary phase as previously described herein. The mobile phase was n-pentane at 210° C. and room temperature split sampling was used. The pressure was held constant at 18 atmosheres for 30 minutes after injection, followed by a linear rise to 36 atmospheres during a 2-hour period. The fluorescence detector excitation and emission wavelengths were set at 300 nm and 360 nm, repectively, for the first 66 minutes. The emission wavelength was then changed to 400 nm for the remainder of the chromatogram in order to obtain better sensitivity for the larger compounds. A 0.10 millimeter slit was placed between the excition source and the capillary column in the detector to reduce the background signal.

Good results were achieved using the 50 meter long pyrex glass tube having an internal diameter of 0.11 millimeter with a bonded phase coating produced as specifically disclosed above using n-pentane as the mobile phase. The initial mobile phase velocity was set at 4 centimeters per second and no changes were made during the run to maintain this linear velocity. This column produced 10,000 plates per meter for a compound with k=0.02 which approaches the efficiencies that are theoretically predicted. This is also equivalent to generating 40 plates per second, which is similar to what is presently achieved by HPLC. Furthermore, the time of analysis is approximately 120 minutes, which is far superior to analysis times presently achievable in caillary HPLC.

On-column fluorometric detection was chosen in order to minimize band broadening often obtained when connecting a capillary to other ancillary equipment, as described in the following articles:

M. Novotny, S. R. Springston, P. A. Peaden, J. C. Fjeldsted and M. L. Lee in Anal. Chem., Vol. 53, pages 407A–414A, 1981.

F. J. Yang in Chromatogr. Commun., Vol. 4, pages 83–85, 1981.

J. W. Jorgensen and K. D. Lukacs in Anal. Chem., Vol. 53, pages 1298–1302, 1981.

This was convenient because the column only needed to be straightened and carefully positioned in the detector light path. Effective detector cell volume of 0.71 $\mu$L, 0.31 $\mu$L and 0.08 $\mu$L were achieved by illuminating a 1 centimeter length of the column of the 0.30 millimeter, 0.20 millimeter and 0.10 millimeter internal diameter capillaries, respectively.

Proper alignment of the column with the excitation source and the emission detection system is important to the detector sensitivity. With pyrex capillaries, the shortest usable excitation wavelength was approximately 280 nm. The background noise was significantly reduced by using a slit of approximately the same width as the inside diameter of the column to direct the excitation beam through the cross-section of the capillary occupied by the mobile phase only. Sensitivities for polycyclic aromatic hydrocarbons using this detector arrangement were on the same order of magnitude as those commonly experienced in capillary gas chromatography using a flame ionization detector. Practical working sample loads were between 10 and 100 ng per component. As in all fluorometric detection systems, the solute quantum efficiencies and the detector wavelengths were major factors affecting solute sensitivity as described by B. S. Das and G. H. Thomas in Anal. Chem., Vol. 50, pages 967–973, 1978.

Values were also obtained using sample loops (valves) with the chromatographic column at 32 atmospheres pressure and 210° C. in all cases. Trichlorobenzene was employed as the sample solvent because its boiling point is higher than 210° C. which allows atmospheric loading of the sample into the valve. For heated valve sampling in which the valve is also heated to 210° C., the 0.5 $\mu$L valve was employed when using 0.30 millimeter internal diameter columns. For smaller diameter columns, the 0.20 $\mu$L valve was used. The reason for this is based on calculations of the contribution of the sample loop volume to band broadening. Assuming a three-fold increase in sample volume upon injection, and calculating the ratio of the peak width due to the sample loop to that due to the column, the data of TABLE II were obtained.

TABLE II

CONTRIBUTION OF SAMPLE LOOP VOLUME TO PEAK WIDTH

| SAMPLE LOOP VOLUME ($\mu$L) | % $w_i/w_c$* COLUMN DIAMETER | | |
|---|---|---|---|
| | 0.30 | 0.20 | 0.10 |
| 0.5 | 8 | 22 | 123 |
| 0.2 | 3 | 9 | 49 |

*The ratio of the peak width due to sample loop volume to peak width due to column volume given in terms of percent.

These figures were calculated for 20 meter long columns, assuming a plate height equal to the column diameter. It was found that when the valve was turned to the injection position and left there for the entire run, an exponential decay was observed in all of the chromatographic peaks, as reported by B. Coq, G. Cretier, J. L. Rocca and M. J. Porthault in J. Chromatogr., Sci., Vol. 19, pages 1–12, 1981. This was especially noticeable for the less retained components. If the valve is left in injecting position for only a few seconds and then return to the sample loading position, this problem was not observed. Evaluating this system with anthracene (k=0.02) gave plate heights of 0.34 millimeter and 0.20 millimeter for 0.30 millimeter and 0.20 millimeter internal diameter columns, respectively.

Room temperature splitting using a 0.20 $\mu$L valve as the sample injecting device gave a plate height of 5 millimeters for coronene on a 0.30 millimeter internal diameter column. Naphthalene gave plate heights of 0.40 millimeter and 0.25 millimeter on 0.30 millimeter and 0.20 millimeter internal diameter columns, respectively. Split ratios of 1:1 and 2:1 were used with these columns and the splitter was kept open continuously throughout the runs.

Both valve sampling systems gave about the same efficiencies for retained components at near optimum mobile phase velocities but differences could be readily seen at high velocities. Using the split system, the observed plate height only doubled in going from 1 centimeter per second to 4 centimeters per second, while heights increased 5 to 6 times for the same increases without splitting. On this basis the use of the split system is preferable since analysis times can be shortened with less loss in resolution. The large increase in plate height at increased velocities with the valve sampling system was probably due to a solvent effect resulting from the difference in sample solvent and mobile phase. This was minimized in the split system because of the dilution of the sample solvent with the mobile phase.

Figure 5:
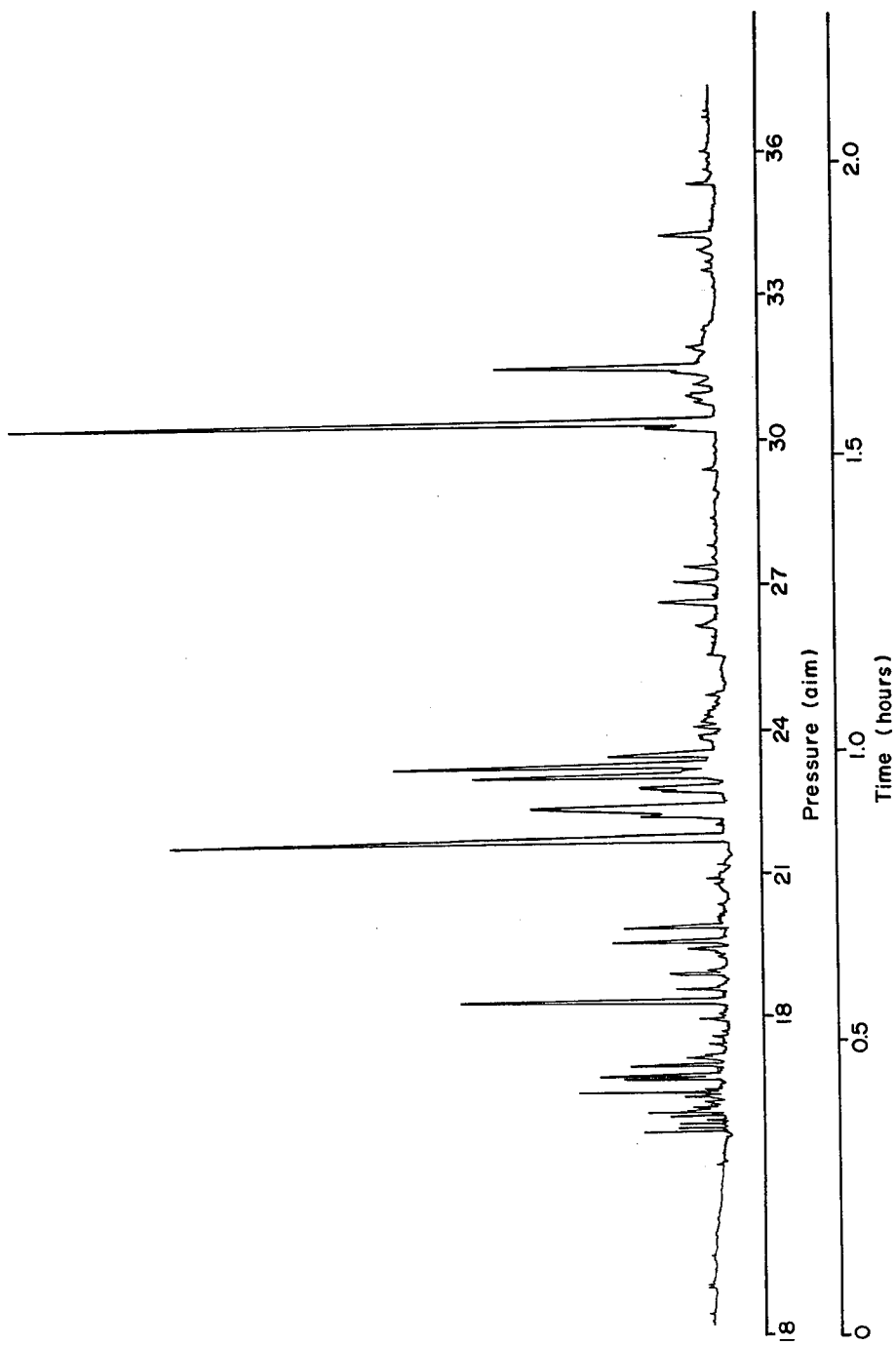
FIG. 5 is a copy of a chromatogram of a coal tar sample obtained on a 50 meter long capillary column having an internal diameter of 0.11 millimeter with injection using supercritical n-pentane as the mobile phase.

FIG. 5 is a copy of the chromatogram obtained on the coal tar sample.

Figure 3:
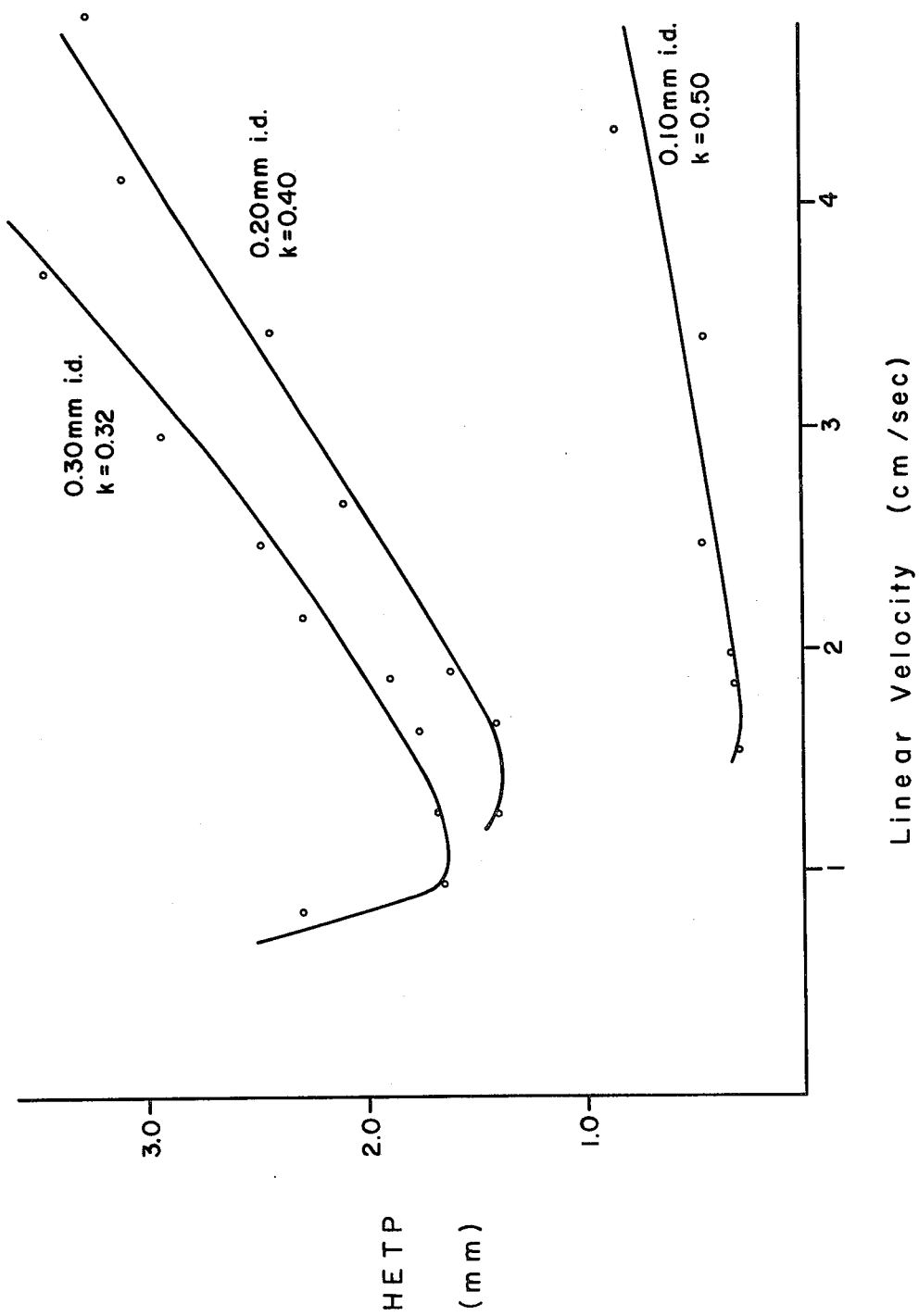
FIG. 3 is a similar van Deemter plot for pyrene.

Using the room temperature split sampling system, a comparison between the 0.30, 0.20 and 0.10 millimeter internal diameter columns was made by constructing the van Deemter plots given in FIGS. 2 and 3 for naphthalene and pyrene. As expected from theory, columns of smaller diameter yield lower plate heights. The shift to lower optimum velocities for higher molecular weight solutes can also be seen by comparing the plots for naphthalene with those for pyrene. This is expected because the diffusion coefficient is smaller for higher molecular weight solutes.

The equation given by M. J. E. Golay in "GAS CHROMATOGRAPHY 1958", D. H. Desty, ed., Academic Press, New York, 1958, pages 36–55, predicts that the minimum plate height for a capillary column should be 0.289 times the column diameter. It was found with the method of the invention that minimum plate heights equal to, or slightly greater than, the column diameters were obtained. This is approximately 3½ times greater than predicted. A significant portion of this is attributable to band-broadening due to sample introduction, and, to some extent, less than ideal efficiency in the particular test, which can be overcome.

The results of the specific examples illustrating the present invention show that a split injection system or a system allowing the use of the same sample solvent as the mobile phase is preferable. Sample concentration at the head of the column as often done in gas chromatography is feasible but better results are obtained with sample loop valving methods. On-column fluorometric detection provides sufficient sensitivity and minimal band broadening. Moreover, the system and process described herein allows the achievement of results close to those predicted by capillary column theory.

While the invention has been described and illustrated with reference to specific embodiments, those skilled in the art will recognize that modifications and variations may be made without departing from the principles of the invention as described hereinabove and as set forth in the following claims.

Having thus described and illustrated the invention what is claimed is:

1. Apparatus for chromatographic analysis which comprises an elongated passageway having inlet and outlet ends and being entirely open between said ends, means for introducing fluid into the inlet end of said passageway, means for removing fluid from said outlet end, means for subjecting fluid in said elongated passageway to temperature and pressure near the critical temperature and pressure of said fluid, means for introducing into said fluid upstream from said inlet end a sample of material to be analyzed chromatographically, and means for subjecting fluid to which said sample has been introduced near or after removal from said outlet end to detection.

2. Apparatus as set forth in claim 1 in which said passageway is a capillary column.

3. Apparatus as set forth in claim 1 in which said means for introducing fluid into said inlet end is a high pressure pump.

4. Apparatus as set forth in claim 1 in which said means for introducing fluid into said inlet end is a high pressure pump operatively connected to an electronic pressure controller/programmer.

5. Apparatus as set forth in claim 1 in which said passageway is a capillary column provided with a coating having an affinity for solute molecules to be analyzed.

6. Apparatus as set forth in claim 5 in which said coating is a polymethylphenylsiloxane polymer.

7. Apparatus as set forth in claim 1 in which said means for introducing sample material into said fluid comprises split injection means.

8. Apparatus as set forth in claim 1 in which said means for introducing sample material into said fluid comprises on-column injection.

9. Apparatus as set forth in claim 1 in which said means for introducing sample material into fluid comprises a sample loop.

10. Apparatus as set forth in claim 1 in which said fluid removal means comprises a restrictor.

11. Apparatus as set forth in claim 10 in which said restrictor comprises a short capillary restrictor connected at one end to said outlet end of said passageway and at the other end to one port of a tee, a second restrictor connected to another port of said tee and a variable high pressure gas regulator connected to the third port of said tee.

12. Apparatus as set forth in claim 1 in which said means for subjecting fluid in said passageway to a temperature near the critical temperature for said fluid comprises a constant temperature oven.

13. Apparatus as set forth in claim 1 in which said means for subjecting said fluid to detection comprises a spectrofluorimeter.

14. Apparatus as set forth in claim 1 in which said means for subjecting said fluid to detection comprises a length of capillary tubing held in position in the beam of a spectrofluorimeter narrowed by a slit to a thickness approximately equal to the internal diameter of the capillary tubing.

15. A method of carrying out the detection of material separated by supercritical fluid chromatography which comprises supplying fluid near its critical point to an elongated passageway having an inlet and an outlet, said passageway being entirely open between said inlet and outlet and being heated between said inlet and outlet near the critical temperature of said fluid, introducing into said fluid upstream from the inlet of said elongated passageway a sample of material to be separated chromatographically, separating said material by supercritical fluid chromatography, and subjecting said fluid near the outlet to detection.

16. A method as set forth in claim 15 in which the step of introducing said sample is carried out by on-column injection.

17. A method as set forth in claim 15 in which the step of introducing said sample is carried out by split injection.

18. A method as set forth in claim 15 in which the step of introducing said sample is carried out by direct injection using suitable valves and solvents.

19. A method as set forth in claim 18 in which said solvent is the same as said fluid.

20. A method as set forth in claim 18 in which the sample is introduced under non-supercritical conditions and thereafter the sample is raised to near the supercritical conditions.

21. A method as set forth in claim 18 in which said detection is carried out by ultra violet detection.

22. A method as set forth in claim 19 in which said detection is carried out by mass spectrometry.

23. A method as set forth in claim 18 in which said detection is carried out by on-column spectrofluorimetric detection near said outlet.

24. A method as set forth in claim 18 in which said detection is carried out by on-column fluorescence detection near said outlet while the fluid is near the supercritical pressure, is in a passageway transparent to said fluorescence and the fluorescent beam is narrowed to a thickness approximately the same as the internal diameter of the transparent passageway.

* * * * *

REEXAMINATION CERTIFICATE (692nd)

United States Patent [19]
Novotny et al.

[11] B1 4,479,380
[45] Certificate Issued Jun. 2, 1987

[54] OPEN-TUBULAR SUPERCRITICAL FLUID CHROMATOGRAPHY

[75] Inventors: Milos Novotny, Bloomington, Ind.; Milton L. Lee, Spanish Fork, Utah; Paul A. Peaden; John C. Fjeldsted, both of Provo, Utah; Stephen R. Springston, Bloomington, Ind.

[73] Assignee: Brigham Young University, Provo, Utah

Reexamination Request:
No. 90/000,926, Dec. 18, 1985
No. 90/000,982, Apr. 10, 1986

Reexamination Certificate for:
Patent No.: 4,479,380
Issued: Oct. 30, 1984
Appl. No.: 352,890
Filed: Feb. 26, 1982

[51] Int. Cl.⁴ .................................................. G01N 30/02
[52] U.S. Cl. .................................................. 73/61.1 C

[56] References Cited

U.S. PATENT DOCUMENTS

4,207,188  6/1980  Tsuda et al. ..................... 210/198.2

OTHER PUBLICATIONS

Balenovic, Z. et al., "Binary Diffusion in Dense Gases to 1360 atm by the Chromatographic Peak-Broadening Method", *J. Chem. Phys.*, 52(2), 915-22 (1970).

Swaid, I. et al., "Determination of Binary Diffusion Coefficients of Benzene and Some Alkyl Benzenes in Supercritical $CO_2$ Between 308 and 328K in the Pressure Range 80 to 160 Bar with Supercritical Fluid Chromatography (SFC)", *Ber. Bunsenges. Phys. Chem.*, 83, 969-74 (1979).

Tsuda, T. et al., "Open-Tubular Microcapillary Liquid Chromatography With 30-40 μm I.D. Columns", *J. Chromatography*, 199, 249-58 (1980).

Novotny, M. et al., "Capillary HPLC: Columns and Related Instrumentation", *J. Chromatography Sci.*, 18, 473-8 (1980).

Ishii, D. et al., "Open Tubular Capillary LC", *J. Chromatography Sci.*, 18, 462-72 (1980).

Peadon, P. A. et al., "High-Performance Liquid Chromatographic Separation of High-Molecular-Weight Polycyclic Aromatic Compounds in Carbon Black", *Anal. Chem.*, 52, 2268-71 (1980).

Myers, M. H. et al., "High-Pressure Gas Chromatography" in *Progress in Separation and Purification*, vol. 3, 133-52 (Wiley-Interscience, New York 1970).

Hartmann "Fluid Chromatography of Styrene Oligomers" Doctoral Dissertation Albert-Ludwig University (Feb.) 1977.

Hirata et al., "Techniques of Liquid Chromatography", *J. Chromatography*, 186: 521-528 (1979).

Randall et al, "Dense Gas Chromatograph/Mass Spectrometer Interface" *Anal. Chem.*, 50(12): 1703-1705 (1978).

Springston et al, "Kinetic Optimization of Capillary Supercritical Fluid Chromatography Using Carbon Dioxide as the Mobile Phase", *Chromatographia* 14(2): 679-684 (1981).

*Primary Examiner*—Stewart J. Levy

[57] ABSTRACT

Apparatus for and method of open-tube supercritical fluid chromatography. The apparatus comprises an elongated passageway having inlet and outlet ends such as a capillary column, coated or not with a coating having affinity for solute molecules to be analyzed, means such as a high-pressure pump operatively connected to an electronic pressure controller/programmer for supplying fluid at high pressure to said inlet end, means such as a flow controller/restrictor for removing fluid from said outlet end, means such as a constant temperature oven for subjecting the fluid between said inlet and outlet ends to a temperature near (below, at or above) the critical temperature of the fluid, means for introducing a sample material into the fluid upstream from the inlet end for chromatographic analysis, such means preferably being an injector of the split injection type or optionally of the on-column type, and means for subjecting fluid to which a sample material has been added to detection by means of an ultraviolet detector, an on-column spectrofluorimeter, a mass spectrometer, and the like. The method comprises carrying out the detection of material after subjecting it to supercritical fluid chromatography in a long stream of fluid, preferably of capillary diameter, having an inlet end and an outlet end and which is subjected between said ends to near supercritical temperature and pressure for the fluid, the detection being carried on the fluid out near the outlet end of any suitable method including ultraviolet detection, spectrofluorimetric detection and mass spectrometric detection.

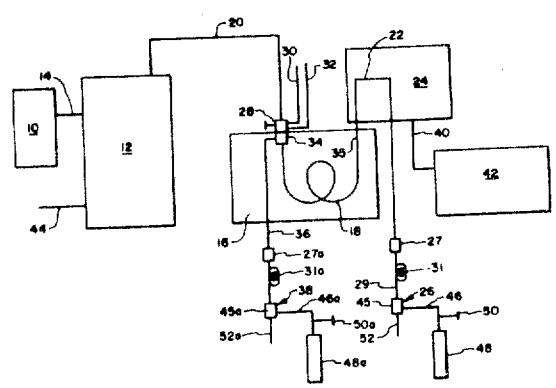

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claims 1 and 15 are determined to be patentable as amended.

Claims 3-14 and 16-24, dependent on an amended claim, are determined to be patentable.

1. Apparatus for chromatographic analysis which comprises an elongated *capillary* passageway *containing a prepared stationary phase and* having inlet and outlet ends and being entirely open between said ends, means for introducing fluid into the inlet end of said passageway, means for removing fluid from said outlet end, means for subjecting fluid in said elongated passageway to temperature and pressure near the critical temperature and pressure of said fluid, means for introducing into said fluid upstream from said inlet end a sample of material to be analyzed chromatographically, and means for subjecting fluid to which said sample has been introduced near or after removal from said outlet end to detection.

15. A method of carrying out the detection of material separated by supercritical fluid chromatography which comprises supplying fluid near its critical point to an elongated *capillary* passageway *containing a prepared stationary phase and* having an inlet and an outlet, said passageway being entirely open between said inlet and outlet and being heated between said inlet and outlet near the critical temperature of said fluid, introducing into said fluid upstream from the inlet of said elongated passageway a sample of material to be separated chromatographically, separating said material by supercritical fluid chromatography, and subjecting said fluid near the outlet to detection.

* * * * *